US00PP22709P2

(12) United States Plant Patent
Bentley

(10) Patent No.: US PP22,709 P2
(45) Date of Patent: May 1, 2012

(54) LAVANDULA PLANT NAMED 'BENTLEY'

(50) Latin Name: *Lavandula stoechas*
Varietal Denomination: Bentley

(76) Inventor: Howard Bentley, Wonga Park (AU)

( * ) Notice: Subject to any disclaimer, the term of this patent is extended or adjusted under 35 U.S.C. 154(b) by 0 days.

(21) Appl. No.: 12/925,025

(22) Filed: Oct. 12, 2010

(51) Int. Cl.
*A01H 5/00* (2006.01)

(52) U.S. Cl. ..... Plt./445
(58) Field of Classification Search ..... Plt./445
See application file for complete search history.

*Primary Examiner* — Kent L Bell

(57) ABSTRACT

A new and distinct *Lavandula* cultivar named 'BENTLEY' is disclosed, characterized by large red-purple terminal bracts, a broad flower spike and a bushy, compact growth habit. The new variety is a *Lavandula,* normally produced as an outdoor ornamental plant for containers or gardens.

1 Drawing Sheet

Latin name of the genus and species: *Lavandula stoechas.*
Variety denomination: 'BENTLEY'.

BACKGROUND OF THE INVENTION

The new cultivar was discovered as a result of a planned breeding program directed by the inventor, Howard Bentley a citizen of Australia. 'Bentley' is a selection arising from the controlled self-pollination of an unnamed, unpatented variety of *Lavandula stoechas.* Parents of the unnamed parent variety are the result of cross-pollination of *Lavandula stoechas* 'Kew Red' (unpatented) as the female parent, and *Lavandula stoechas* 'Pukehou' (unpatented) as the male. Cross-pollination of the grandparent plants took place in Park Orchards, Victoria, Australia in November 2001. From this cross the F1 generation was raised in February 2002 and grown to flowering maturity in September 2002. At this stage the F1 generation was self-pollinated and the seed sown in February 2003. From these F2 seedlings a selection was made of the seedling now referred to as 'Bentley' in September 2004, by the inventor in a research nursery in Wonga Park, Australia.

Asexual reproduction of the new cultivar 'BENTLEY' was first performed the Spring of 2005, by vegetative cuttings at a research nursery in Wonga Park, Australia. Multiple generations have since been produced and have shown that the unique features of this cultivar are stable and reproduced true to type in successive generations.

SUMMARY OF THE INVENTION

The cultivar 'BENTLEY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BENTLEY' These characteristics in combination distinguish 'BENTLEY' as a new and distinct *Lavandula* cultivar:

1. Red-Purple terminal bracts.
2. Large terminal bracts
3. Bushy, compact plant habit.

PARENT COMPARISON

Plants of the new cultivar 'BENTLEY' are similar to plants of the parent, *Lavandula stoechas* 'Kew Red' in most horticultural characteristics, however, plants of the new cultivar 'BENTLEY' have significantly longer sterile terminal bracts, more sterile terminal bracts and an overall wider inflorescence than the seed parent. Additionally, plants of 'Bentley' are slightly larger than 'Kew Red' and have more branches, producing a denser plant.

Plants of the new cultivar 'BENTLEY' are similar to plants of the parent, *Lavandula stoechas* Pukehou' in most horticultural characteristics, however, plants of the new cultivar 'BENTLEY' have different colored sterile terminal bracts. Additionally, plants of 'BENTLEY' are slightly larger than 'Pukehou' and have many more branches, producing a denser plant.

COMMERCIAL COMPARISON

'BENTLEY' can be compared to the commercial variety *Lavandula stoechas* 'Sugarberry Ruffles' U.S. Plant Pat. No. 18,243. The two varieties are similar in many horticultural characteristics, however, plants of 'BENTLEY' differ in producing sterile terminal bracts of a lighter color and wider inflorescence. Additionally, plants of 'BENTLEY' are denser, with more branches and have longer peduncles.

BRIEF DESCRIPTION OF THE PHOTOGRAPH

The accompanying photograph in FIG. 1 illustrates in full color a typical plant of 'BENTLEY' grown outdoors in Victoria, Canada, in a 20 cm container. Age of the plant photographed is approximately 35 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'BENTLEY' plants grown outdoors in a hobbyist garden in Victoria, Canada. The growing temperature ranged from 10° C. to 30° C. daytime and 7° to 20° C. at night. No growth regulators or other chemical treatments were used. Measurements and numerical values represent averages of typical plant types.

Botanical classification: *Lavandula stoechas* 'BENTLEY'

PROPAGATION

Time to initiate roots: About 14 to 21 days at approximately 20-24° C.
Root description: Fibrous
Propagation method: Vegetative cuttings

PLANT

Age of plant described: Approximately 35 weeks from a rooted cutting
Growth habit: Bushy, compact.
Pot size of plant described: 20 cm
Height: Average: 50 cm.
Plant spread: Average: 60 cm.
Growth rate: Moderate
Main stem color: Near RHS Green 138C
Main stem texture: Pubescent
Stem length: Approximately 45 cm
Stem diameter: Approximately 0.8 cm
Branching characteristics: Very free branching.
Length of branches: Average 7 cm.
Quantity of branches per plant: More than 50
Characteristics of branches:
- *Form.*—Quadrangular.
- *Diameter.*—Average 0.3 cm.
- *Color.*—Near RHS Green 138C.
- *Texture.*—Pubescent.
- *Strength.*—Moderately strong and flexible.
- *Internode length.*—Average: 0.7 cm.

FOLIAGE

Leaf:
- *Arrangement.*—Opposite, simple.
- *Average length.*—Approximately 2.7 cm.
- *Average width.*—Approximately 0.4 cm.
- *Shape of blade.*—Linear.
- *Apex.*—Murcronate.
- *Base.*—Cuneate.
- *Attachment.*—Sessile.
- *Margin.*—Entire.
- *Texture of top surface.*—Slightly pubescent.
- *Texture of bottom surface.*—Smooth.
- *Leaf internode length.*—Approximately 0.4 cm.
- *Color.*—Young foliage upper side: Near R.H.S. Green 136D. Young foliage under side: Near RHS Green 138C. Mature foliage upper side: Near RHS Green 138C. Mature foliage under side: Near RHS Green 138C.
- *Venation.*—Type: Reticulate. Venation color upper side: Near RHS Green 136D. Venation color under side: Near RHS Green 136D.

FLOWER

Bloom period: Naturally blooming profusely mid Spring through mid-Summer. Moderate reblooming in the Fall.

Inflorescence:
- *Form.*—Small single flower in verticillasters arranged in spikes. 9 to 11 rows of flowers. Flowers have small bracts, and large showy terminal bracts. Approximately 150 inflorescences per plant.
- *Individual flowers.*—Singly occurring, 30 to 50 flowers and buds per inflorescence. Florets: Corolla tube is 2-lipped. Size individual flowers: Length: Approximately 0.5 cm. Diameter: Approximately 0.3 cm.
- *Inflorescence size, excluding terminal bracts.*—Length: Approximately 4.9 cm. Width: Approximately 3.0 cm.
- *Corolla.*—Color: Immature both surfaces: Near RHS Red-Purple 72A. Mature both surfaces: Near RHS Red-Purple 72B. Fading both surfaces: Near RHS Red-Purple 74D. Lip/Lobe Description: Shape: Obovate. Length: approximately 0.4 cm. Width: approximately 0.3 cm. Apex: Obtuse. Margin: Entire. Texture, both surfaces: Glabrous, papery.
- *Spike description.*—Length: Approximately 4.9 cm. Width: Approximately 2.0 cm. Color: Near Red-Purple 72A.
- *Flower bud description.*—Shape: Cylindric. Length: approximately 0.3 cm. Width: approximately 0.1 cm. Color: Near Greyed-Purple N187D.

Terminal bracts:
- *Quantity.*—4 to 6.
- *Length.*—Approximately 3.9 cm.
- *Width.*—Approximately 2.1 cm.
- *Aspect.*—Undulating.
- *Margin.*—Entire.
- *Apex.*—Obtuse.
- *Base.*—Rounded.
- *Texture, both surfaces.*—Glabrous, papery.
- *Duration on plant.*—Approximately 6 weeks, with good color. Persistent.
- *Color.*—Upper side of immature bract: Near RHS Red-Purple 74C. Under side of immature bract: Near RHS Red-Purple 74C. Upper side of mature bract: Near RHS Red-Purple 74C. Under side of mature bract: Near RHS Red-Purple 74C. Bract color fading to: Near RHS Red-Purple 74D.

Small bracts:
- *Quantity.*—Typically 2.
- *Length.*—Approximately 1.0 cm.
- *Width.*—Approximately 0.7 cm.
- *Apex.*—Shallow bi-lobe.
- *Margin.*—Entire.
- *Base.*—Obtuse.
- *Aspect.*—Undulating.
- *Duration on plant.*—Approximately 6 weeks. Persistent. Color: Upper side of immature bract: Near RHS Red-Purple 72C, center stripe near Red-Purple 71A. Under side of immature bract: Near RHS Red-Purple 72C, center stripe near Red-Purple 71A. Upper side of mature bract: Near RHS Red-Purple 72C. Under side of mature bract: Near RHS Red-Purple 72C. Bract color fading to: Near RHS Red-Purple 73C.

Fragrance: Strong Lavender scent.
Flowers: Self-cleaning.
Calyx:
- *Sepal description.*—Shape: Fused into tube. Quantity: 5. Length: approximately 0.2 cm. Width: approximately 0.2 cm. Apex: Acute. Margin: Entire. Texture, both surfaces: Pubescent, velvety.

Peduncle:

*Peduncle length.*—Average range approximately 7 to 9 cm.

*Peduncle diameter.*—Approximately 0.4 cm.

*Aspect.*—Upright.

*Color.*—Near RHS Green 138C.

REPRODUCTIVE ORGANS

Androecium:

*Stamens.*—4.

*Anther shape.*—Linear.

*Anther length.*—Approximately 0.05 cm.

*Anther color.*—Near RHS Yellow 7A.

*Pollen quantity.*—Minimal.

*Pollen quantity.*—Near RHS Yellow 4A.

OTHER CHARACTERISTICS

Seeds and fruits: Not observed to date.

Disease/pest resistance: Neither resistance nor susceptibility to pathogens and pests common to *Lavandula* have been observed.

Temperature tolerance: The new variety tolerates temperatures between 10 to 40° C.

What is claimed is:

1. A new and distinct cultivar of *Lavandula* plant named 'BENTLEY' as herein illustrated and described.

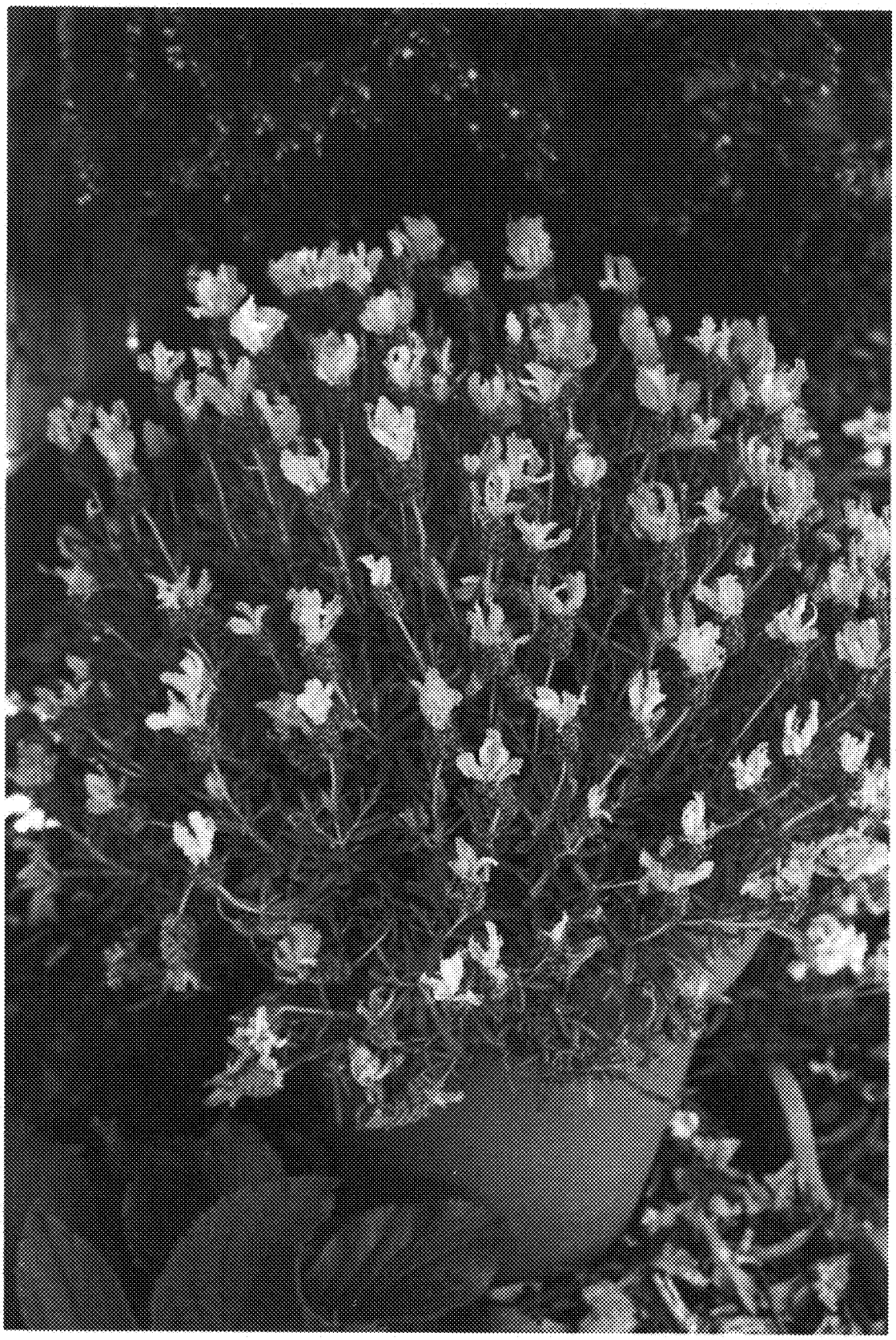

* * * * *